US006929475B1

(12) United States Patent
Dragan

(10) Patent No.: US 6,929,475 B1
(45) Date of Patent: Aug. 16, 2005

(54) PRE-DOSED APPLICATOR AND APPLICATOR SYSTEM

(75) Inventor: William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 10/264,921

(22) Filed: Oct. 4, 2002

(51) Int. Cl.[7] ........................ A61C 5/04
(52) U.S. Cl. ........................ 433/89; 401/119
(58) Field of Search ........................ 433/80, 89, 90; 604/1, 2, 218; 401/119

(56) References Cited

U.S. PATENT DOCUMENTS 3,863,654 A 2/1975 Morane et al.
4,997,371 A * 3/1991 Fischer ........................ 433/90
5,286,257 A * 2/1994 Fischer ........................ 604/82
5,660,273 A 8/1997 Discko, Jr.
6,059,570 A 5/2000 Dragan et al.
D435,105 S 12/2000 Dragan et al.
6,186,792 B1 2/2001 Discko
6,288,138 B1 9/2001 Yamamoto et al.
6,290,503 B1 9/2001 Lemon et al.
6,328,159 B1 12/2001 Discko, Jr.
6,386,872 B1 * 5/2002 Mukasa et al. ............... 433/90
D458,456 S 6/2002 Dragan et al.
D461,247 S 8/2002 Dragan et al.
6,450,717 B1 9/2002 Salz et al. .................. 401/125

FOREIGN PATENT DOCUMENTS

EP 1147 74 746 A1 11/2001

* cited by examiner

*Primary Examiner*—Melba Bumgarner
(74) *Attorney, Agent, or Firm*—Fattibene & Fattibene; Paul A. Fattibene; Arthur T. Fattibene

(57) ABSTRACT

An applicator for applying a material such as a chemical or a medicament. A material to be applied is placed on an absorbent portion of the applicator, such as a flocked end, sponge or foam, brush, or other equivalent absorbent substance. After drying, the material is in an inactive stable state on the applicator. When desired, the inactive stable material is activated by water or other solvent. In another embodiment, a package containing an applicator end having a pre-dosed dry inactive stable material is combined with a second material so that a two-part or multi-component material may be easily dispensed and activated. The package containing the first and second component may be a tray, a capsule, or a tip end syringe. The pre-dosed single use applicator may be used to apply a variety of materials, such as chemicals or medicaments, to the surface or site desired without complicated and messy mixing or cross-contamination.

9 Claims, 5 Drawing Sheets

40
38
50
52
44
48
42
46

10
12
14
16
18

110
112
114
116
118

210
212
214
216
218

210A
212A
214A
216A
218A
219

22
24
26
210'
216'
218'
220

310
314
312
318

34
12
10
32
18
36

28
30

40
38
50
52
44
48
42
46

PRE-DOSED APPLICATOR AND APPLICATOR SYSTEM

FIELD OF THE INVENTION

The present invention relates in general to the application of a material with an applicator, and particularly to the application of a chemical or medicament to a patient using a single dose pre-dosed applicator.

BACKGROUND OF THE INVENTION

Many materials such as chemicals and medicaments are applied with an applicator. Typically, the material to be applied is contained in bulk form, such as a bottle or jar into which the applicator is dipped. The applicator is then moved to the area on which the material is to be applied. In many medical and dental applications, the use of such bulk containers of material is disadvantageous in that cross contamination between patients can result. Often, when more material is needed during a medical procedure, the applicator is re-dipped in the bulk container.

Many of the materials to be applied are in liquid form and may drip or spill when the applicator is dipped into a bulk container. This is messy and may even result in a hazardous condition should the materials spilled be hazardous. Additionally, some materials may stain and be difficult to clean up.

Accordingly, there is a need for a simple, easy to use, pre-dosed single use applicator in which the material can be applied easily without the possibility of cross contamination.

SUMMARY OF THE INVENTION

The present invention relates to an applicator pre-dosed with a material, such as a chemical or a medicament. The material is placed on an absorbent portion of the applicator and permitted to dry. The material is then in an inactive, stable state on the applicator. The material on the applicator is re-activated upon being exposed to water, saliva, liquids, or other activating materials.

In another embodiment of the invention, a package is provided containing an applicator with a stable, inactive first material thereon and a separate reservoir of an activating second material. The activating second material reacts with the stable, inactive first material to produce a reaction or beneficial result.

Accordingly, it is an object of the present invention to provide a pre-dosed, single use applicator that is easy to use.

It is yet another object of the present invention to prevent cross contaminations between uses or patients.

It is an advantage of the present invention that the applicator or container is in a stable, inactive state on an applicator ready to be activated.

It is a feature of the present invention that material is dried on an applicator.

These and other objects, advantages, and features will become more readily apparent in view of the following detailed description.

DETAILED DESCRIPTION OF THE PREFERRED EMBODIMENTS

Figure 1:
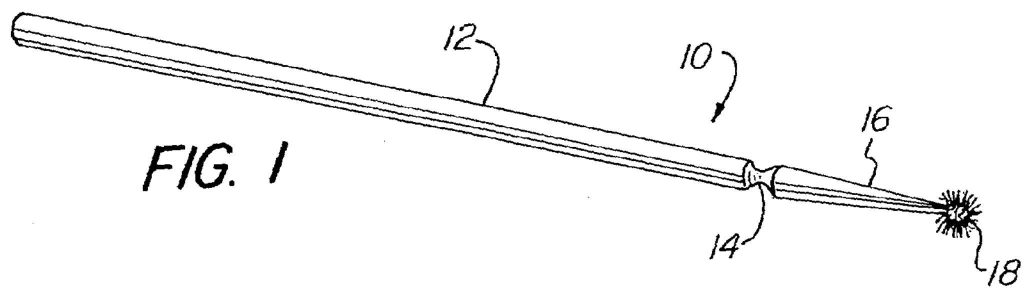
FIG. 1 is a perspective view of an applicator having a flocked end.

FIG. 1 illustrates a pre-dosed applicator 10 having a handle 12 and a hinge or neck 14. Adjacent hinge or neck 14 is a tapered end 16 terminating in a flocked applicator end 18. The flocked applicator end 18 contains a multitude or plurality of flocks, hairs, or small bristles adhered to the tapered end 16. The tapered end 16 may have a ball at the end. The flocked applicator end 18 is pre-dosed with a material by dipping or otherwise coating the flock 18 with a liquid material and permitting the liquid to dry to an inactive state. After drying, the material is rendered stable and inactive, ready to be re-activated. The inactive material may be re-activated with a second activating material or upon exposure to a solvent or moisture at the site to be applied.

For example, in dentistry, an indicating liquid is often used to detect caries or decay in teeth. The indicating liquid is a dye which, when placed onto tooth decay and rinsed off, will stain any areas that are diseased or decayed. The dye is often messy and can permanently stain many unintended surfaces. The indicating material may be dried onto the flock 18. The indicating material is then re-activated by exposure to water or saliva, or other solvent. Any material that may be dried and re-activated may be used on the pre-dosed applicator.

Figure 2:
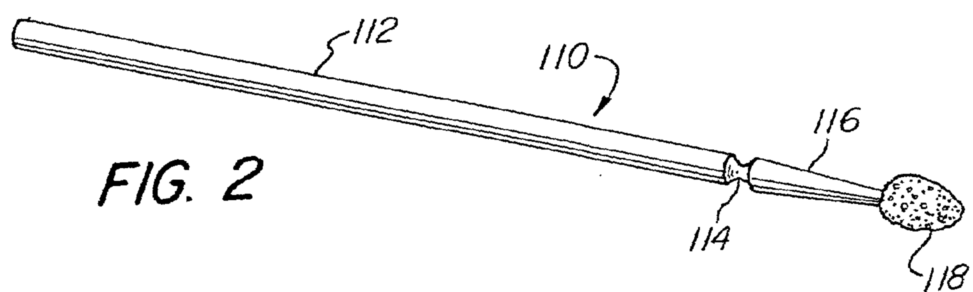
FIG. 2 is a perspective view of an applicator having a foam end.

FIG. 2 illustrates another embodiment of the present invention using a foam applicator end. The pre-dosed foam applicator 110 has a handle 112 and a hinge or neck 114. Adjacent the hinge or neck 114 is a tapered end 116. Attached to the tapered end 116 is a foam applicator 118. The hinge 114 permits the tapered end 116 to be bent or angled relative to the axis of the handle 112. This helps in the positioning of the foam applicator end 118. The foam applicator end 118, as in the embodiment illustrated in FIG. 1, is pre-dosed with a material that is dried and capable of being re-activated. The foam applicator end 118 may also be made of other absorbent materials such as cotton, fabric, or any other equivalent absorbent material capable of holding a liquid material that is dried and re-activated.

Figure 3:
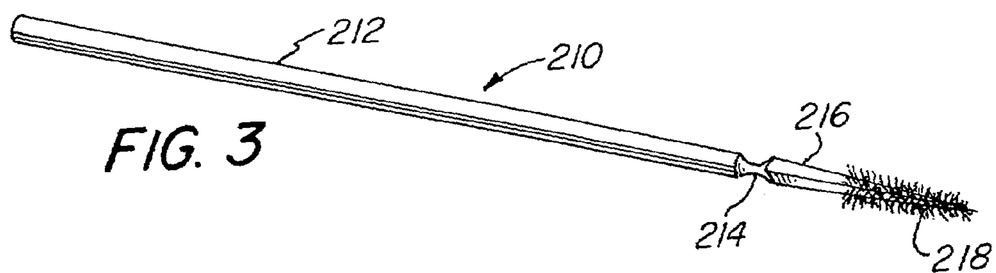
FIG. 3 is a perspective view of an applicator having an elongated flocked end.

FIG. 3 is another embodiment of the present invention that may be utilized as a dental wedge, toothpick, or gum or gingival stimulator. The pre-dosed wedge applicator 210 comprises a handle 212 with a hinge or neck 214. Adjacent the hinge or neck 214 is a tapered end 216. A flock 218 is adhered to a substantial portion of the tapered end 216. The longitudinal extent of the flocked wedge portion 218 is at least the width of a tooth or approximately 0.25 to 2.00 centimeters.

The flocked wedge portion 218 may be pre-dosed with an astringent or hemostatic agent. The astringent or hemostatic agent, after drying, becomes stable and inactive. The flocked portion 218 may also be pre-dosed with an abrasive, such as zirconium silicate. In this embodiment the applicator 210 may be used as a substitute for dental floss to clean between the teeth. The flocked wedge portion 218 may also be impregnated with an abrasive material.

The flocked portion 218 may also be pre-dosed with an antiseptic, antibiotic, or analgesic material. Of course, the flocked portion 218 may be any absorbent substance capable of absorbing or holding the dry material to be later re-activated. For example, the absorbent substance may be flock, cotton, foam, bristles, or any other substantially equivalent absorbent substance.

Figure 3A:
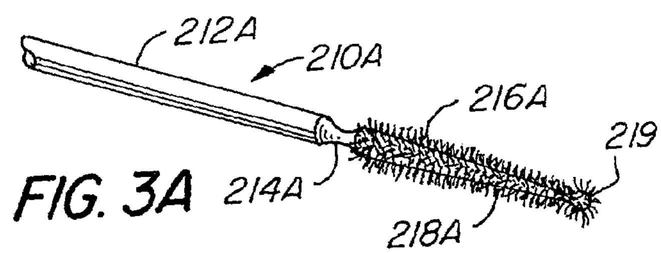
FIG. 3A is a partial perspective view of an applicator having an elongated flocked end with a ball tip.

FIG. 3A illustrates another embodiment of the present invention having a ball end. The pre-dosed applicator 210A comprises a handle 212A with a hinge or neck 214A. Adjacent the hinge or neck 214A is a tapered end 216A. The tapered end in this embodiment is rounded or an elongated cone. A flock 218A is adhered to a substantial portion of the tapered end 216A. The longitudinal extent of the flocked wedge portion 218A is at least the width of a tooth, or approximately between one and two centimeters. A ball 219 is placed on the end of the tapered end 216A. The ball 219 prevents injury to the gingival or gums. The flocked wedge may also be used as a tooth cleaner, toothpick or gingival stimulator. When used as a toothpick or gingival stimulator, the wedge shaped applicator may be pre-dosed with flavors, disinfectants, antiseptics, antibiotics, analgesics, or other similar equivalent materials. When used as a toothpick or gingival stimulator the flocked wedge portion or tapered end 216A is used to clean between the teeth without any pre-dosed material. The flock 218A preferably extends from the distal end at ball 219 to the neck 214A. The neck 214A facilitates bending the tapered end 216A.

Figure 4:
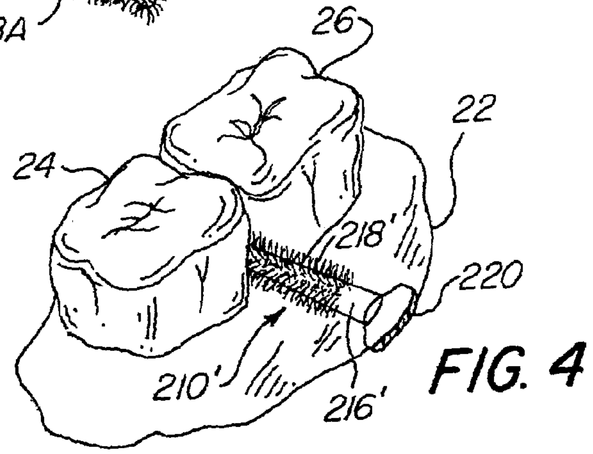
FIG. 4 illustrates the application of a wedge shaped flocked embodiment of the present invention.

FIG. 4 illustrates the application of another embodiment of a wedge applicator in use. The wedge applicator 210' comprises a flocked wedge portion 218' placed on a wedge shaped portion 216'. A handle 220 may be used to facilitate insertion and removal of the wedge applicator 210'. The wedge applicator 210' is placed between the teeth 24 and 26. Gingiva, tissue, or gum 22 is adjacent the base of the teeth 24 and 26.

A pre-dosed wedge is beneficial in many dental procedures. Wedges are typically used in dentistry. Wedges are used in class two cavity preparation restorations. In a class two cavity, adjacent sides of the back or posterior teeth are involved. Upon the removal of decay, it is necessary to use a matrix band to contain the stored material. The matrix band is a band of metal surrounding the tooth. A wedge is used to hold the matrix band against the bottom of the cavity preparation. This prevents excess filling material from being forced behind the prepared cavity. Improperly positioned matrix bands can result in a restoration that is susceptible to periodontal infections or other problems. It is often advantageous to keep the preparation dry during placement of the restorative material. A flocked wedge pre-dosed with an astringent or hemostatic agent, when in position, is reactivated and aids in keeping the gum lines clear and the prepared cavity preparation dry. The natural absorbency of the flocked material will aid in keeping the preparation dry. Additionally, the flocked wedge or tapered end may be used without any pre-dosed material or astringent or hemostatic agent.

Figure 5:
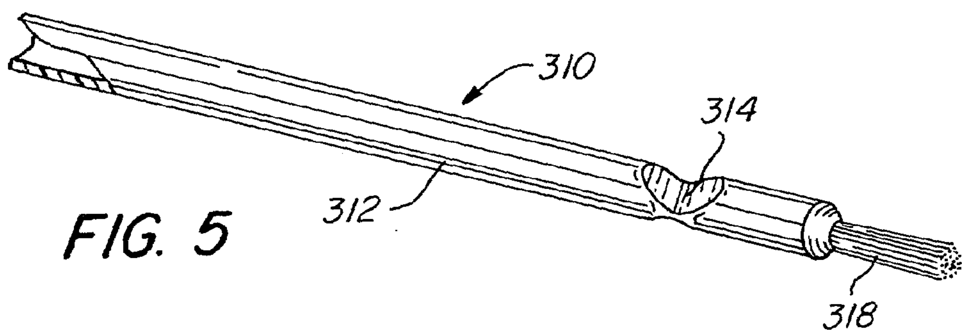
FIG. 5 is a perspective view of an applicator having a brush end.

FIG. 5 illustrates another embodiment of a pre-dosed brush applicator 310. This embodiment comprises a handle 312, a hinge or a crimp 314 placed adjacent an end portion having a brush 318 formed therein. The brush 318 may be pre-dosed with an inactive stable material. The material may then be re-activated for use or to apply the re-activated material.

Figure 6:
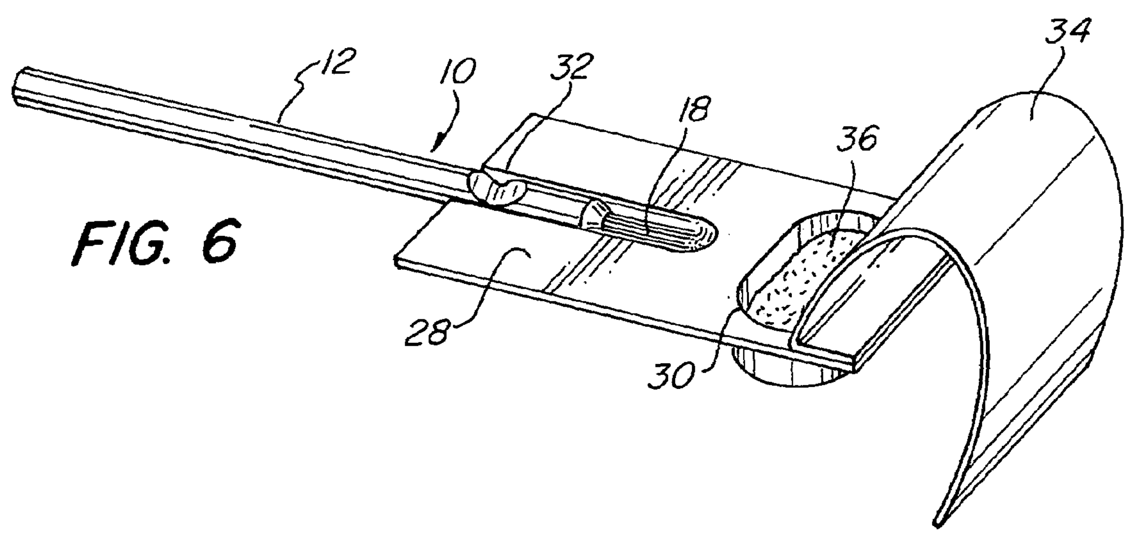
FIG. 6 is a perspective view illustrating a package containing a first inactive material on an applicator and a separate second activating material.

FIG. 6 illustrates another embodiment of the present invention illustrating a package having an inactive first material and an activating second material. A pre-dosed applicator 10 having a handle 12 is placed within a tray 28. The tray 28 has an applicator well 32 and a material well 36 formed therein. The tray 28 may be made of an suitable plastic material. The applicator 10 is held within the applicator well 32 of tray 28 and has an applicator end 18 that is pre-dosed with a first inactive stable material. The applicator end 18 may be a brush as illustrated, or a flock, sponge, or other equivalent material. The activating material well 30 contains an activating second material 36. A cover 34 may be used to seal the top surface of tray 28 protecting the pre-dosed applicator 10 and the second activating material 36.

In use, the pre-dosed applicator 10, which is pre-dosed with an inactive stable material on the applicator end 18, is removed from the tray 28 and dipped into the activating second material 36. The activating second material 36 works in cooperation with the first initially inactive stable material on the applicator end 18 of the pre-dosed applicator 10 so as to when activated and combined result in forming an activated material with the desired properties. The activating second material 36 may be a solvent such as alcohol, acetone or any another chemical agent that has a reaction with the first initially stable inactive material on the applicator end 118 of the pre-dosed applicator 10. Accordingly, many two-part component materials may be conveniently packaged and used in a single dose applicator.

Figure 7:
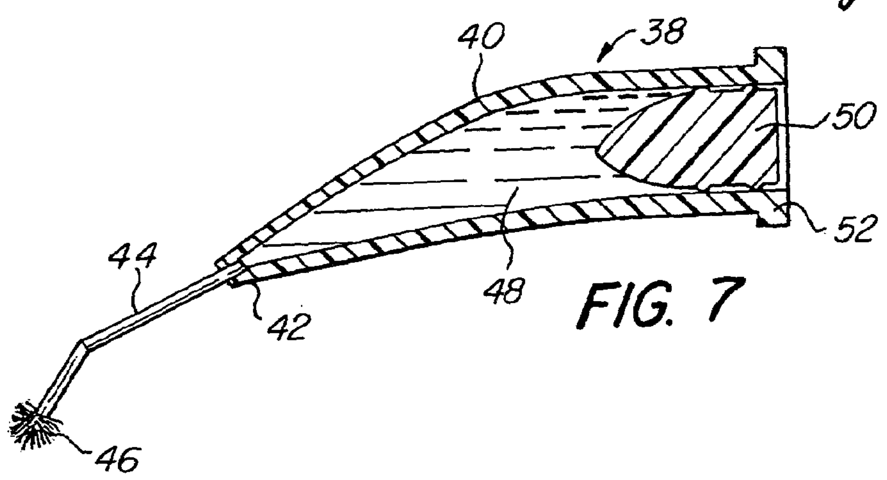
FIG. 7 is a cross section illustrating a capsule having a first inactive material on an applicator and a separate reservoir of an activating second material.
Figure 8:
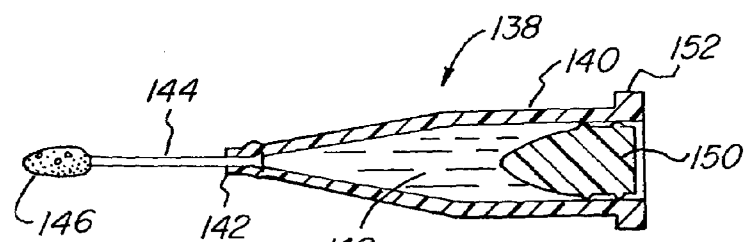
FIG. 8 is a cross section of another embodiment of a capsule of the present invention having a foam applicator end.
Figure 9:
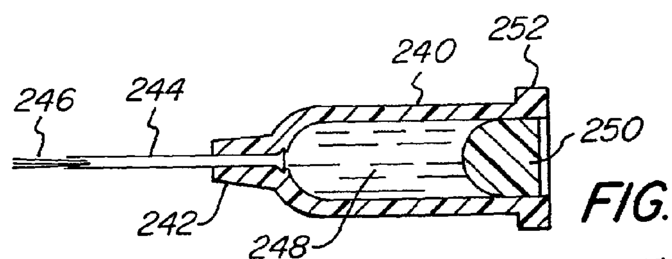
FIG. 9 is a cross section of another embodiment of a capsule of the present invention having a brush applicator end.

FIGS. 7–9 are cross-sections of capsule embodiments of the present invention. FIG. 7 is a cross section of a capsule embodiment of the present invention. Capsule 38 comprises a body 40 having a discharge end 42. Placed in the discharge end 42 is a cannula 44. Cannula 44 is preferably made of a malleable metal. A flocked applicator end 46 is placed on the distal end of the cannula 44. The flocked applicator end 46 is pre-dosed with a first stable inactive material. A second activating material 48 is placed within the body 40 of capsule 38. A piston 50 seals the rearward open end of the body 40. A flange 52 is placed adjacent the open end of body 40 so as to attach to a dispenser, not illustrated. In this embodiment, upon advancing piston 50, the second activating material 48 is dispensed through cannula 44 and through the flocked applicator end 46, combining with the inactive stable material on the flocked applicator end 46. Accordingly, two component or two-part materials may be dispensed easily without any pre-mixing.

FIG. 8 is a cross section of another embodiment of a capsule 138. Capsule 138 has a body 140 with a discharge end 142. Placed within discharge end 142 is a cannula 144. Attached to cannula 144 is a foam applicator 146. The open end of the body 140 is sealed with a piston 150. Adjacent the open end of body 140 is a flange 152. A second activating material 148 is placed within the body 140. The co-action of the first material contained within the foam applicator end 146 and the second material 148 contained within the body 140 results in the two material being combined and activated, having a desired therapeutic effect.

FIG. 9 is yet another embodiment of a capsule of the present invention. Capsule 238 comprises a body 240 having a discharge end 242 with a cannula 244 placed therein. Within cannula 244 are bristles 246 forming a bristle brush. The open end of the body 240 is sealed with a piston 250. The bristles 246 are pre-dosed with a stable inactive first material. The body 240 contains a second stable inactive material 248. Upon advancing the piston 250 towards the discharge end 242, the second material 248 is forced through cannula 244 and through bristles 246. The combining of the first and second materials results in activation of the materials to obtain a desired action.

There are many well-known two-part materials that when combined or mixed form a desired reaction. Such materials may be sealants, adhesives, hemostatic agents, whitening agents, and numerous other equivalent two-part materials that when combined form a material having desired properties.

Figure 10:
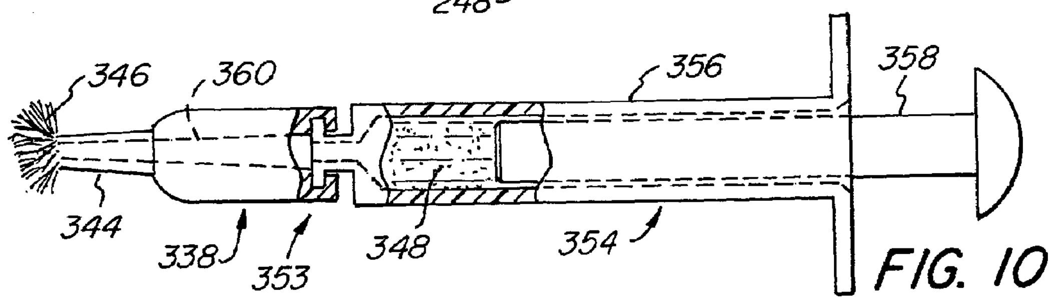
FIG. 10 schematically illustrates another embodiment of the present invention utilizing an applicator tip and a syringe.

FIG. 10 illustrates another embodiment of the present invention. In this embodiment, an empty tip 338 may be attached to a syringe 354 by an attachment means 353. The mating or attachment means 353 of the empty tip 338 and the syringe 354 may be accomplished by any equivalent known attachment structure, such as a Luhr lock conventionally used on syringes. The tip 338 may also simply be press-fit onto the discharge end 352 of the syringe 354. Threads or a bayonet type structure may also be used as means for attaching the tip 338 to the syringe 354. Other equivalent attachment means may be used to hold the tip 338 onto the syringe 354.

The tip 338 comprises a discharge end or nozzle 344 having a flocked applicator end 346. The flocked applicator end 346 contains a first stable inactive material. A bore 360 placed within the tip 338 communicates to the open discharge end of the syringe 354. The syringe 354 has a syringe body 356 and a syringe plunger 358. Contained within the syringe 354 is a second material 348.

In use, the second material 348 may be contained in bulk in the syringe 354. The empty tip 338 may then be placed or attached onto the syringe 354 with the second material 348 being dispensed through the bore 360 within the tip 338. The second material contacts the pre-dosed flocked applicator end 346 containing a first material. This results in a co-action of the two materials to activate the materials producing a desired result or reaction. In this embodiment, multiple empty tips 338 may be combined with use of a single bulk syringe 354. Therefore, the single bulk syringe 354 may contain a number of doses to be dispensed with a plurality of empty tips 338 having a pre-dosed flocked applicator end 346.

Figure 10A:
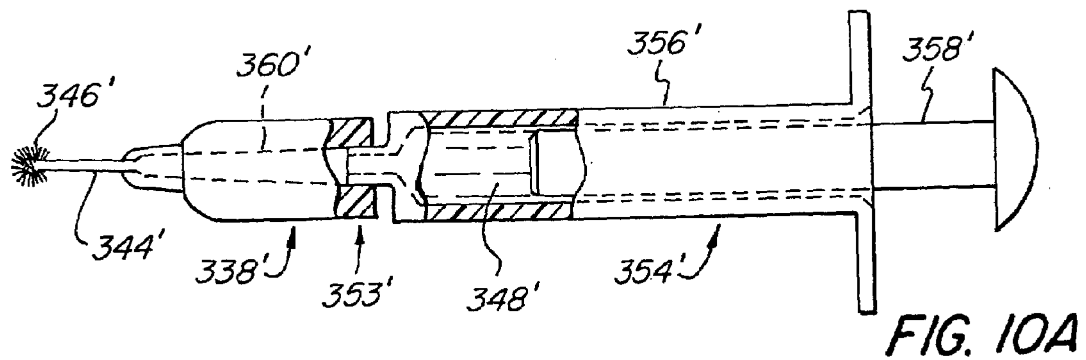
FIG. 10A schematically illustrates another embodiment of the present invention utilizing an applicator tip and a syringe.

FIG. 10A illustrates another embodiment of the present invention. In this embodiment, an empty tip 338' may be attached to a syringe 354' by an attachment means 353'. In this embodiment the attachment means 353' is a press-fit. Other equivalent attachment means may be used to hold the tip 338' onto the syringe 354'.

The tip 338' comprises a cannula discharge end 344' having a flocked applicator end 346'. The cannula discharge end 344' may be made of a soft ductile metal that may be easily bent into a position. The flocked applicator end 346' contains a first stable inactive material therein. A bore 360' placed within the tip 338' communicates to the open discharge end of the syringe 354'. The syringe 354' has a syringe body 356' and a syringe plunger 358'. Contained within the syringe 354' is a second material 348'.

Figure 11A:
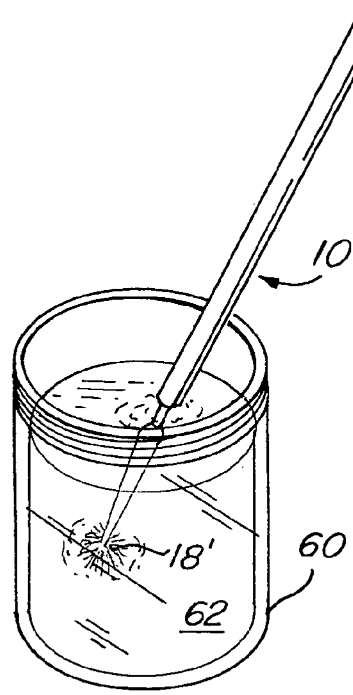
FIGS. 11A–D schematically illustrates the preparation of an embodiment of the present invention.
Figure 11B:
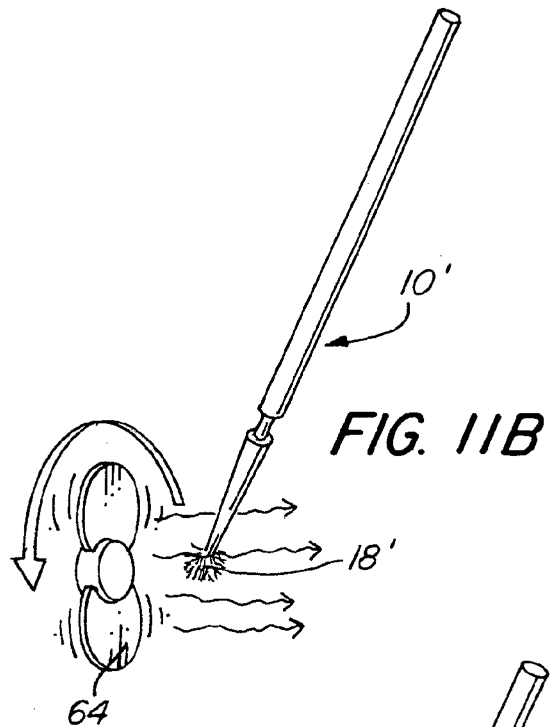
Figure 11C:
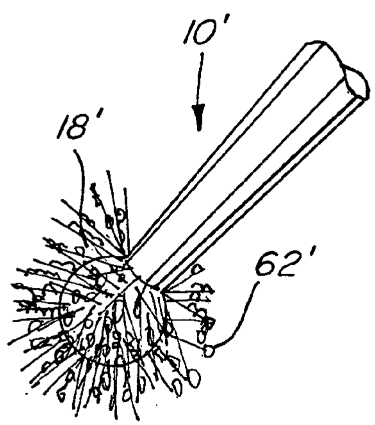
Figure 11D:
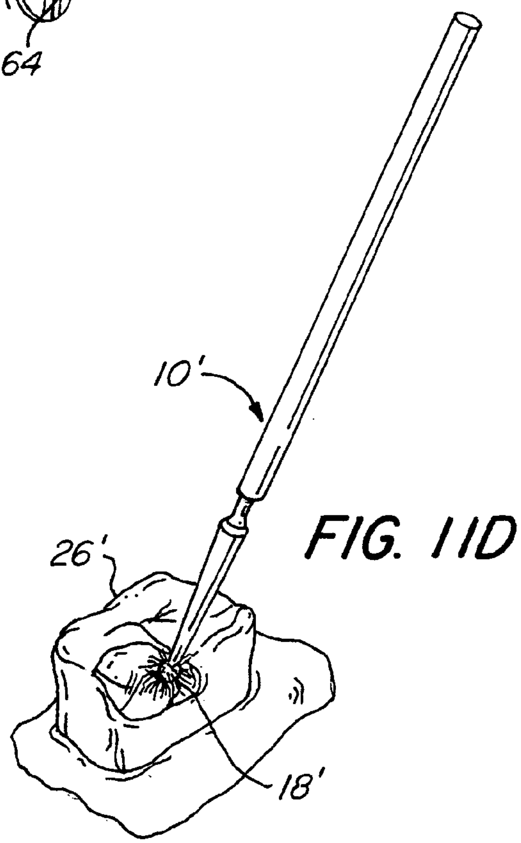

FIGS. 11A–D schematically illustrate the manufacturing process for making an embodiment of the present invention. FIG. 11A illustrates dipping an applicator 10' into a container 60 holding a solution or suspension 62 containing a material intended to be applied with the applicator 10'. The flocked end 18' of the applicator 10' absorbs a portion of the solution or suspension containing the material. FIG. 11B illustrates drying the dipped flocked end 18'. A fan 64 may be used to dry the flocked end 18' of applicator 10'. FIG. 11C illustrates the flocked end 18' of the applicator 10' having dried material 62' from the solution or suspension contained within the flocked end 18'. When desired the material 62' in the flocked end 18' may be reactivated and applied. The material 62' may be reactivated by dipping the flocked end 18' into a solvent for the material 62' or may be reactivated in the environment in which the applicator 10' is used. For example, saliva in a patient's mouth may activate the material 62' to be applied to a tooth. FIG. 11D illustrates applying the material on the flocked end 18' of the dosed applicator 10' to a tooth 26'. While FIGS. 11A–D illustrate the use of an applicator 10' having a flocked end 18', any equivalent type of applicator may be used. For example, a brush, sponge, or cotton swab type applicator may be used.

Figure 12:
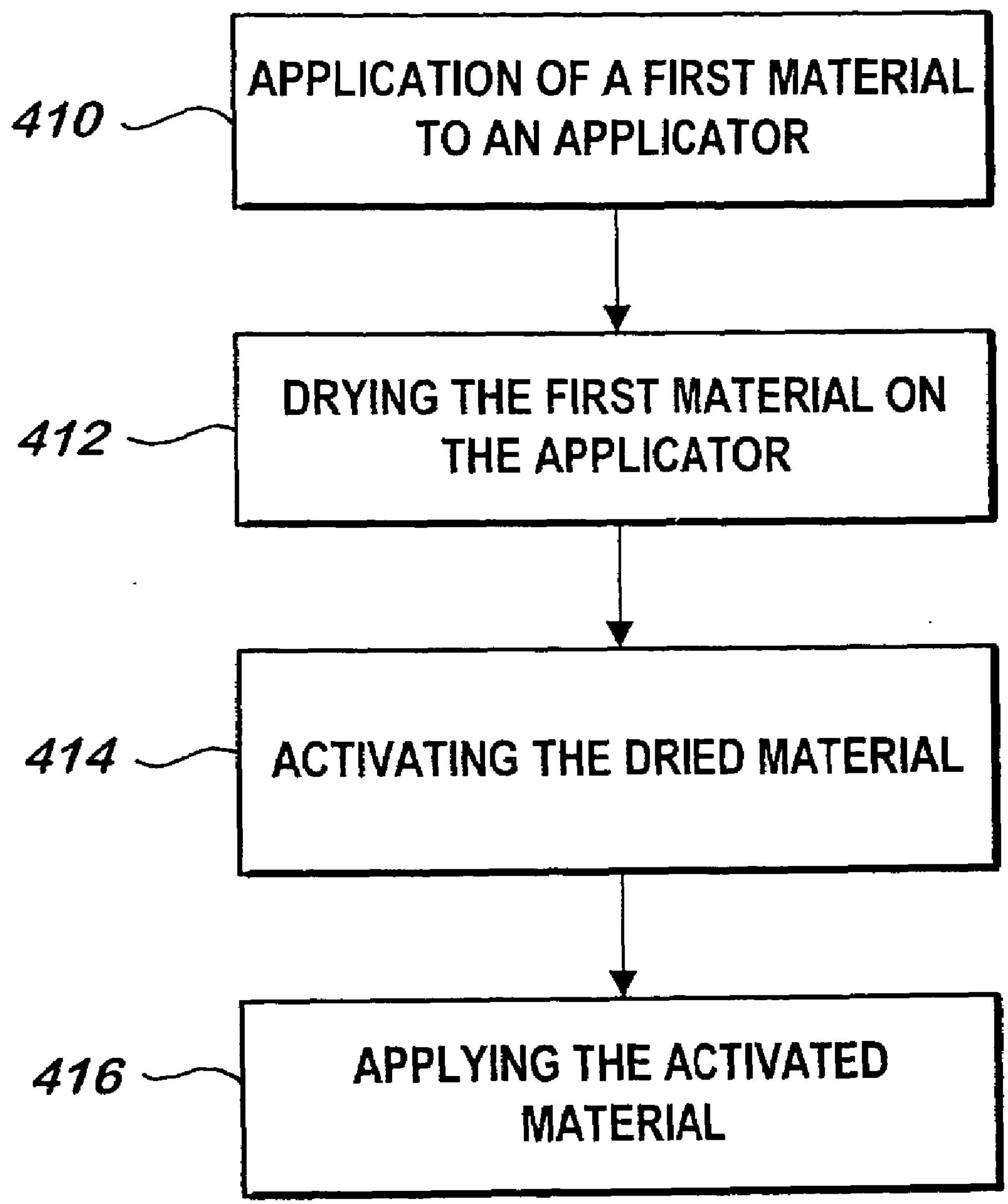
FIG. 12 is a block diagram illustrating the method steps of the present invention.

FIG. 12 illustrates the method steps in an embodiment of the present invention. Box 410 represents the step of applying a first material to an applicator. Box 412 represents the method step of drying the material on the applicator. Box 414 represents the method step of activating the dried material. Box 416 represents the step of applying the activated material.

Accordingly, although the preferred embodiments have been illustrated and described, it will be obvious to those skilled in the art that various modifications may be made without departing from the spirit and scope of this invention.

What is claimed is:

1. A pre-dosed application system for dispensing material with multiple components comprising:

a cannula having a bore and a discharge end;

an absorbent substance applicator portion pre-dosed with a first dry inactive material attached to said cannula adjacent the discharge end; and a container coupled to the bore of said cannula opposite the discharge end, said container containing a second activating material, whereby when the first dry inactive material is combined with the second activating material a desired material is formed.

2. A pre-dosed application system for dispensing material with multiple components as in claim 1 wherein:

said container comprises a capsule attached to said cannula.

3. A pre-dosed application system for dispensing material with multiple components as in claim 1 wherein:

the absorbent substance applicator portion is selected from the group consisting of flock, foam, bristles, and cotton.

4. A pre-dosed application system for dispensing material with multiple components as in claim 1 wherein:

said container comprises a syringe.

5. A pre-dosed application system for dispensing material with multiple components as in claim 4 wherein:

the absorbent substance applicator portion is selected from the group consisting of flock, foam, bristles, and cotton.

6. A pre-dosed application system for dispensing material with multiple components comprising:

a capsule having an open rear end and a discharge end;

a piston placed within the open rear end;

a cannula having an applicator end, said cannula attached to the discharge end of said capsule;

an absorbent substance placed on the applicator end of said cannula;

a first dry inactive material contained within said absorbent substance; and a second activating material placed within said capsule, whereby when the first dry inactive material is combined with the second activating material upon advancing said piston a desired material is formed.

7. A pre-dosed application system for dispensing material with multiple components as in claim 6 wherein:

the absorbent substance is selected from the group consisting of flock, foam, bristles, and cotton.

8. A pre-dosed application system for dispensing material with multiple components as in claim 6 wherein:

said cannula comprises metal.

9. A pre-dosed application system for dispensing material with multiple components as in claim 6 further comprising:

means, formed on said capsule, for attaching said capsule to a dispenser.

* * * * *